United States Patent
Perry et al.

(10) Patent No.: US 7,399,711 B2
(45) Date of Patent: * Jul. 15, 2008

(54) METHOD FOR CONTROLLING A RECESS ETCH PROCESS

(75) Inventors: Andrew J. Perry, Fremont, CA (US); Vijayakumar C. Venugopal, Berkeley, CA (US)

(73) Assignee: Lam Research Corporation, Fremont, CA (US)

( * ) Notice: Subject to any disclaimer, the term of this patent is extended or adjusted under 35 U.S.C. 154(b) by 350 days.

This patent is subject to a terminal disclaimer.

(21) Appl. No.: 10/286,409

(22) Filed: Nov. 1, 2002

(65) Prior Publication Data

US 2004/0087041 A1    May 6, 2004

Related U.S. Application Data

(60) Provisional application No. 60/408,619, filed on Sep. 6, 2002, provisional application No. 60/403,213, filed on Aug. 13, 2002.

(51) Int. Cl.
*H01I 21/302* (2006.01)
(52) U.S. Cl. .............. 438/714; 438/7; 438/8; 438/9; 438/16; 216/60
(58) Field of Classification Search ........... 438/7, 438/8, 9, 16, 714; 216/60
See application file for complete search history.

(56) References Cited

U.S. PATENT DOCUMENTS

| | | | |
|---|---|---|---|
| 4,147,435 A | 4/1979 | Habegger | |
| 5,900,633 A | 5/1999 | Solomon et al. | |
| 5,936,734 A | 8/1999 | Johs et al. | |

(Continued)

FOREIGN PATENT DOCUMENTS

| EP | 1111356 A2 | 6/2001 |
|---|---|---|
| JP | 2000292129 | * 10/2000 |

OTHER PUBLICATIONS

Hicks et al., "Reflectance Modeling for In Situ Dry Etch Monitoring of Bulk SiO$_2$ and III-V multilayer structures" (Nov. 1994) Jrnl of Vac. Sc. & Tech. pp. 3306-3310.

Bosch-Charpenay et al., "Real-Time Etch-Dept Measurements of MEMS Devices" (Apr. 2002) Jrnl of MicroElect. Sys., IEEE, NY, pp. 111-117.

(Continued)

*Primary Examiner*—George A. Goudreau
(74) *Attorney, Agent, or Firm*—IP Strategy Group, P.C.

(57) ABSTRACT

A method of controlling a recess etch process for a multilayered substrate having a trench therein and a column of material deposited in the trench includes determining a first dimension from a surface of the substrate to a reference point in the substrate by obtaining a measured net reflectance of at least a portion of the substrate including the trench, computing a modeled net reflectance of the portion of the substrate as a weighted incoherent sum of reflectances from $n \geq 1$ different regions constituting the portion of the substrate, determining a set of parameters that provides a close match between the measured net reflectance and the modeled net reflectance, and extracting the first dimension from the set of parameters; computing an endpoint of the process as a function of the first dimension and a desired recess depth measured from the reference point; and etching down from a surface of the column of material until the endpoint is reached.

21 Claims, 13 Drawing Sheets

U.S. PATENT DOCUMENTS

| | | | |
|---|---|---|---|
| 5,980,768 | A | 11/1999 | Abraham |
| 6,111,634 | A | 8/2000 | Pecen et al. |
| 6,136,712 | A | 10/2000 | Klippert et al. |
| 6,160,621 | A | 12/2000 | Perry et al. |
| 6,271,047 | B1 | 8/2001 | Ushio et al. |
| 6,275,297 | B1 | 8/2001 | Zalicki |
| 6,410,451 | B2 | 6/2002 | Nguyen et al. |
| 6,413,867 | B1* | 7/2002 | Sarfaty et al. ............... 438/689 |
| 6,567,213 | B2 | 5/2003 | Rosencwaig et al. |
| 6,589,869 | B2* | 7/2003 | Sarfaty et al. ............... 438/689 |
| 6,608,681 | B2 | 8/2003 | Tanaka et al. |
| 6,673,637 | B2 | 1/2004 | Wack et al. |
| 6,979,578 | B2* | 12/2005 | Venugopal ................... 438/14 |
| 7,019,844 | B2* | 3/2006 | Venugopal et al. .......... 356/504 |

OTHER PUBLICATIONS

Benson et al., "In-situ Spectroscopic Reflectometry for Polycrystalline Silicon Thin Film Etch Rate Determination during Reactive Ion Etching", (Jun. 1996) Jrnl of Elect. Mat., pp. 955-964.

Anon., "Zero-Order reflecting Reference Optics", (Jan. 1990) IBM Tech. Discl. Bulletin, pp. 381-383.

PCT International Search Report, PCT/US03/25146, dated Feb. 20, 2004.

P.A. Heimann and R.J. Schutz, "Optical etch-rate monitoring: computer simulation of reflectance," J. Electrochem. Soc. 131, pp. 881-885 (1984).

P.A. Heimann, "Optical etch-rate monitoring using active device areas: lateral interference effects," J. Electrochem. Soc. 132, pp. 2003-2006 (1985).

H.L. Maynard, N. Layadi, and J.T.-C. Lee, "Multiwavelength ellipsometry for real-time process control of the plasma etching of patterned samples," J. Vac. Sci. Technol. B 15, pp. 109-115 (1997).

W. Kong, H.-T. Huang, and F. L. Terry, Jr., "A hybrid analysis of ellipsometry data from patterned structures," Proceedings of NIST 2000, AIP Conference Proceedings, v. 550, pp. 373-377 (2001).

P. Lalanne and D.L. Lalanne, "On the effective medium theory of subwavelenght periodic structures," J. Mod. Opt. (1996).

V. C. Venugopal, A. Lakhtakia, R. Messier, and J.-P. Kucera, "Low permittivity nonocomposite materials using sculptured thin film technology," J. Vac. Sci. Technol. A 18, pp. 32-36 (2000).

G. Bouchitte and R. Petit, "Homogenization techniques as applied in the electromagnetic theory of gratings," Electromagnetics 5, pp. 17-36 (1985).

Z. R. Hatab, J.R. McNeil, and S. S. H. Naqvi, "Sixteen-megabit dynamic random access memeory trench depth characterization using two-dimensional diffraction analysis," J. Vac. Sci. Technol. B 13, pp. 174-182 (1995).

H. Kikuta, Y. Ohira, H. Kubo, and K. Iwata, "Effective medium theory of two-dimensional subwavelength gratings in the non-quasistatic limit," J. Opt. Soc. of A., vol. 15, No. 6, pp. 1577-1585 (Jun. 1998).

J.P. Merceron, V.C. Venugopal, A.J. Perry, and A.J. Miller, "Endpoint Strategies for Recess Processes in DRAM and eDRAM Applications," Abstract 1253, AVS 49th International Symposium (Nov. 2002).

S. Zaidi, G. Stojakovic, A. Gutmann, C. Bozdog, U. Mantz, S. B. Charpenay, and P. Rosenthal, "FTIR-based non-destructive method for metrology of depths in poly silicon filled trenches," Metrology, Inspection, and Process Control for Microlithography XVII, Daniel J. Herr (ed.), Proceedings of SPIE, vol. 5038, pp. 185-190 (2003).

C. G. Galarza, P. P. Khargonekar, F. L. Terry, Jr., "Real-time estimation of patterned wafer parameters using in-situ spectroscopic ellipsometry," Proceedings of the 1999 IEEE, International Conference on Control Applications, Hawaii, pp. 773-778 (Aug. 1999).

J. Merceron, "Robust endpoint strategies for recess processes," Ecole Polytechnique Promotion X99, pp. 1-28, (2002).

B. Michel, "Recent developments in the homogenization of linear bianisotropic composite materials," *Electromagnetic Fields in Unconventional Materials and Structures* (Chapter 2), Singh and Lakhtakia (ed.), John Wiley and Sons, Inc., pp. 39-83 (2000).

P.-Y. Guittet, U. Mantz, P. Weidner, J.-L. Stehle, S. Bourtault, and D. Zahorski, "Infrared Spectroscopic ellipsometry in semiconductor manufacturing," Metrology, Inspection, and Process Control for Microlithography XVIII, R. M. Silver (ed.), Proceedings of SPIE, vol. 5375, pp. 771-778 (May 2004).

A. Dag, V. M. Rubinstein, Y. Gilboa, S. Hedayati, "Performing STI process control using large-spot-size fourier-transform reflectometry," micromagazine.com, pp. 25-30 (Apr. 2003).

C. F. Bohren and D. R. Huffman, *Absorption and Scattering of Light by Small Particles* Wiley Science Paperback Series, John Wiley and Sons, Inc., pp. 212-219 (1983).

U.S. Appl. No. 10/286,410, filed Nov. 1, 2002, "Method for in-situ monitoring of patterned substrate processing using reflectometry".

U.S. Appl. No. 10/401,118, filed Mar. 27, 2003, "Process Endpoint Detection Method Using Broadband Reflectometry".

Bosch-Charpenay et al., "Real-Time Etch-Depth Measurements of MEMS Devices", Jrnl of Microelectromechanical Systems, IEEE INC, NY, US, vol. 11, No. 2, Apr. 2002, pp. 111-117.

Singapore Written Opinion, App No. 200500812-3, Danish Patent & Trademark Office, Mailed Feb. 11, 2006, 10 pp.

Chinese Office Action, App No. 03819341.8, dated Mar. 24, 2006, State Intellectual Property Office of P.R.C. pp. 1-8.

Bosch-Charpeney, "Real-Time Etch-Depth Measurements of MEMS Devices", (XP001125204), (Apr. 2002) Jrnl of Micro Electromech. Sys., IEEE Inc., NY, vol. 11/2, pp. 111-117.

Exam Report mailed Nov. 22, 2006 from European Patent Office re EP application 03785204.4, 7 pp.

A. Lakhtakia (ed.), "Cakes and Pastries, and Linear Optical Composite Materials Too," Selected Papers on Linear Optical Composite Materials, Sep. 1995, pp. xiii-xxiv, Milestone vol. 120, SPIE Optical Engineering Press (1996), Bellingham, WA.

J. C. Maxwell Garnett, "XII. Colours in metal Glasses and in Metallic Films," Selected Papers on Linear Optical Composite Materials, Jun. 2, 1904, pp. 121-138, Milestone vol. 120, SPIE Optical Engineering Press (1996), Bellingham, WA.

Von D.A.G. Bruggeman, "Berechnung Verschiedener Physikalischer Konstanten von Heterogenen Substanzen," Selected Papers on Linear Optical Composite Materials, Sep. 1936, pp. 200-221, Milestone vol. 120, SPIE Optical Engineering Press (1996), Bellingham, WA (Not Translated).

D.E. Aspens, "Local-Field Effects and Effective-Medium Theory: A Microscopic Perspective," Selected Papers on Linear Optical Composite Materials, Aug. 1982, pp. 222-227, Milestone vol. 120, SPIE Optical Engineering Press (1996), Bellingham, WA.

G. B. Smith, "Effective Medium Theory and Angular Dispersion of Optical Constants in Films With Oblique Columnar Structure," Selected Papers on Linear Optical Composite Materials, Oct. 1988, pp. 663-668, Milestone vol. 120, SPIE Optical Engineering Press (1996), Bellingham, WA.

S. M. Rytov, "Electromagnetic Properties of a Finely Stratified Medium," Selected Papers on Subwavelength Diffractive Optics, Nov. 1955, pp. 3-12, Milestone vol. 166, SPIE Optical Engineering Press (2001), Bellingham, WA.

R. C. McPhedran et al., "Lossy Lameliar Gratings in the Quasistatic Limit," Selected Papers on Subwavelength Diffractive Optics, Mar. 1981, pp. 56-79, Milestone vol. 166, SPIE Optical Engineering Press (2001), Bellingham, WA.

Philippe Lalanne, "On the Effective Medium Theory of Subwavelength Periodic Structures," Selected Papers on Subwavelength Diffractive Optics, Oct. 1995, pp. 104-126, Milestone vol. 166, SPIE Optical Engineering Press (2001), Bellingham, WA.

F. T. Chem et al., "Diffractive Phase Elements Based on Two-Dimensional Artificial Dielectrics," Selected Papers on Subwavelength Diffractive Optics, Oct. 1994, pp. 401-403, pp. 104-126, Milestone vol. 166, SPIE Optical Engineering Press (2001), Bellingham, WA.

Singapore Examination Report, App No. 200500812-3, IPOS (Intellectual Property Office of Singapore), Mailed Dec. 11, 2006, 10 pp.

* cited by examiner

METHOD FOR CONTROLLING A RECESS ETCH PROCESS

CROSS REFERENCE TO RELATED APPLICATIONS

This application claims priority from and incorporates by reference the following provisional application(s) entitled "Endpoint Strategies for in situ Control of Recess and Deep Trench Etch Processes," filed "Aug. 13, 2002" (Application No. 60/403,213) by inventor(s) Vijayakumar C. Venugopal and Andrew J. Perry and "Reflectrometry-based Approaches For in situ Monitoring of Etch Depths in Plasma Etching Processes," filed Sep. 6, 2002 (Application No. 60/408,619) by inventor(s) Vijay C. Venugopal and Andrew J. Perry.

BACKGROUND OF THE INVENTION

The invention relates generally to methods for monitoring and controlling processes used in forming features on patterned substrates, such as semiconductor substrates. More specifically, the invention relates to a method for detecting an endpoint in a recess etch process.

Recess etch processes are used in fabricating semiconductor devices such as dynamic random access memory (DRAM) and embedded DRAM (eDRAM). DRAMs and eDRAMs store information in integrated circuits that contain capacitors. FIG. 1A shows a typical storage node 100 of a DRAM cell. The storage node 100 includes a deep trench 102 formed in a patterned semiconductor substrate 104. A column of polysilicon 106 is formed in the deep trench 102, and a recess 108 is provided above the column of polysilicon 106. The recess 108 may be lined with an insulation material (not shown) so as to isolate the polysilicon 106 from structures, such as transfer devices, above. The trench 102 typically has a high aspect ratio. In the current technology, for example, the depth of the trench 102 is typically several microns deep, while the width of the trench 102 is typically on the order of 300 nm. As advances are made in integration technology, the width of the trench is expected to get even smaller, e.g., shrink down to 90-100 nm.

FIG. 1B shows the semiconductor substrate 104 prior to forming the deep trench (102 in FIG. 1A). In a typical configuration, the semiconductor substrate 104 includes a substrate layer 110, typically made of silicon, a dielectric layer 112, typically made of silicon dioxide, and a mask layer 114, typically made of silicon nitride. The semiconductor substrate 104 is coated with a thin-film of photoresist mask 116. Before forming the trench, an area 115 of the photoresist mask 116 where the trench will be formed is removed, causing the underlying layers to become exposed. The semiconductor substrate 104 is then placed in a process chamber (not shown), such as a plasma chamber, and the trench is etched through the exposed underlying layers and into the substrate. After etching the trench, the remaining photoresist mask 116 is removed.

FIG. 1C shows the semiconductor substrate 104 after etching the trench 102 and removing the photoresist mask (116 in FIG. 1B). In the figure, the trench 102 is filled with polysilicon 106. As the trench 102 is filled with polysilicon, a blanket of polysilicon 120 is also formed on the top surface of the semiconductor substrate 104, i.e., over the mask layer 114. Typically, a small dish (or depression) 122 also appears above the opening of the trench 102 as a consequence of the filling process. To facilitate etching of a recess in the column of polysilicon 106 in the trench 102, the blanket of polysilicon 120 is then removed (or planarized), as shown in FIG. 1D. The planarized surface 123 can be produced by a process such as planar layer etching or chemical-mechanical polishing. It should be noted that all or only a portion of the blanket of polysilicon (120 in FIG. 1C) may be removed during the planarization process. After planarizing the blanket of polysilicon, the column of polysilicon 106 in the trench 102 is etched down to a predetermined depth to form the recess (108 in FIG. 1A).

Various modifications can be made to the sequence of processes described above to form different recess structures. For example, as shown in FIG. 1E, the trench 102 can be initially lined with a dielectric material 124, such as an oxide. Polysilicon 106 can then be deposited into the lined trench 102 and on top of the mask layer 114, as previously described. The blanket of polysilicon 120 on the mask layer 114 can be planarized, and the column of polysilicon 106 can be etched down to form a lined recess (126 in FIG. 1F). This process may be used to create a buried polysilicon strap, for example. In another example, as shown in FIG. 1G, the column of polysilicon 106 in the trench 102 can be etched to form a recess 128. The recess 128 can then be filled with a dielectric material 130, such as an oxide. Another etching process can be used to remove a portion of the dielectric material 130 so as to form a dielectric liner (132 in FIG. 1H) that extends partly down the trench 102.

In most applications, the depth of the recess relative to a reference point in the semiconductor substrate, such as the bottom of the sacrificial mask layer, is a critical dimension. Thus, the ability to accurately determine how far down to etch the column of polysilicon in the trench to achieve the desired recess depth is very important. Various factors make it challenging to form a recess of a desired depth in the trench. For example, the opening of the trench through which the recess will be etched is very tiny, and the scale of the depression above the column of polysilicon in the trench can easily be on the same order as the accuracy or even the absolute depth of the recess to be etched. Perhaps even more challenging are the incoming material variations from one substrate to another, e.g., the variations in the thickness of the mask layer and the depth of the depression above the column of polysilicon in the trench. Without knowing these variations, it would be difficult to accurately determine how far down to etch the column of polysilicon to make the required recess depth.

What is desired therefore is a method for detecting an endpoint in a recess etch process by monitoring the absolute recess depth that takes into account such factors as incoming material variations.

SUMMARY OF THE INVENTION

In one aspect, the invention relates to a method of controlling a recess etch process. For a multilayered substrate having a trench therein and a column of material deposited in the trench, the method comprises determining a first dimension from a surface of the substrate to a reference point in the substrate by obtaining a measured net reflectance spectrum of at least a portion of the substrate including the trench, computing a modeled net reflectance spectrum of the portion of the substrate as a weighted incoherent sum of reflectances from $n \geq 1$ different regions constituting the portion of the substrate, determining a set of parameters that provides a close match between the measured net reflectance spectrum and the modeled net reflectance spectrum, and extracting the first dimension from the set of parameters. The method further includes computing an endpoint of the recess etch process as a function of the first dimension and a desired recess depth measured from the reference point and etching down from a surface of the column of material until the endpoint is reached.

In another aspect, the invention relates to a method of controlling a recess etch process which comprises planarizing a surface of a multilayered substrate having a trench therein and a column of material deposited in the trench. The method further includes determining a first dimension from the surface of the substrate to a reference point in the substrate after planarizing. The first dimension is determined by obtaining a measured net reflectance spectrum of at least a portion of the substrate including the trench, computing a modeled net reflectance spectrum of the portion of the substrate as a weighted incoherent sum of reflectances from $n \geq 1$ different regions constituting the portion of the substrate, wherein the reflectance of each of the n different regions is a weighted coherent sum of reflected fields from $k \geq 1$ laterally-distinct areas constituting the region, determining a set of parameters that provides a close match between the measured net reflectance spectrum and the modeled net reflectance spectrum, and extracting the first dimension from the set of parameters. The method further includes computing an endpoint of the recess etch process as a function of the first dimension and a desired recess depth measured from the reference point and etching down from a surface of the column of material until the endpoint is reached.

In yet another aspect, the invention relates to a method of controlling a recess etch process for a multilayered substrate having a trench therein and a column of material deposited in the trench. The method comprises determining a first dimension from a surface of the substrate to a reference point in the substrate and a second dimension from the surface of the substrate to a surface of the column of material. The first and second dimensions are determined by obtaining a measured net reflectance spectrum of at least a portion of the substrate including the trench, computing a modeled net reflectance spectrum of the portion of the substrate as a weighted incoherent sum of reflectances from $n \geq 1$ different regions constituting the portion of the substrate, determining a set of parameters that provides a close match between the measured net reflectance spectrum and the modeled net reflectance spectrum, and extracting the first and second dimensions from the set of parameters. The method further includes computing an endpoint of the recess etch process as a function of the first and second dimensions and a desired recess depth measured from the reference point and etching down from a surface of the column of material until the endpoint is reached.

These and other features and advantages of the invention will be discussed in more detail in the following detailed description of the invention and in conjunction with the following figures.

BRIEF DESCRIPTION OF THE DRAWINGS

The invention is illustrated by way of example, and not by way of limitation, in the figures accompanying the drawings, and in which like reference numerals refer to similar elements, and in which.

DETAILED DESCRIPTION OF THE PREFERRED EMBODIMENTS

The invention will now be described in detail with reference to a few preferred embodiments, as illustrated in the accompanying drawings. In the following description, numerous specific details are set forth in order to provide a thorough understanding of the invention. It will be apparent, however, to one skilled in the art, that the invention may be practiced without some or all of these specific details. In other instances, well-known process steps and/or features have not been described in detail in order to not unnecessarily obscure the invention. The features and advantages of the invention may be better understood with reference to the drawings and discussions that follow.

The invention provides a robust and reliable method for determining an endpoint in a recess etch process. The method of the invention can be divided into two major steps. In one embodiment, the first step includes estimating in-situ incoming material variations. This estimation step compensates for variations, such as differences in mask layer thicknesses, starting etch depths, and position and orientation of the substrate or differences in pattern density from one substrate to another. The first step allows the determination of the absolute vertical dimension of the column of material to be removed.

The second step includes using single- or multi-wavelength interferometry to monitor the actual etching of the recess. The interferometric endpoint detection method involves determining the number of fringes required to reach the desired recess depth. The number of fringes can be determined accurately once the absolute vertical dimension of the column of material to be removed and the starting etch depth are known.

In one embodiment, the invention uses broadband reflectometry to estimate the incoming material variations. In one embodiment, the method for estimating the incoming material variations involves measuring a reflectance spectrum of the semiconductor substrate. The physical parameters of interest are estimated by matching the measured reflectance spectrum to a modeled reflectance spectrum of the semiconductor substrate. In accordance with one embodiment of the invention, a model for calculating the reflectance spectrum of the semiconductor substrate is provided. Advantageously, the model does not place any restrictions on arrangement of features on the semiconductor substrate, i.e., the model is not limited to a semiconductor substrate having special test features and can be applied to a semiconductor substrate having a complex array of random features.

Figure 1A:
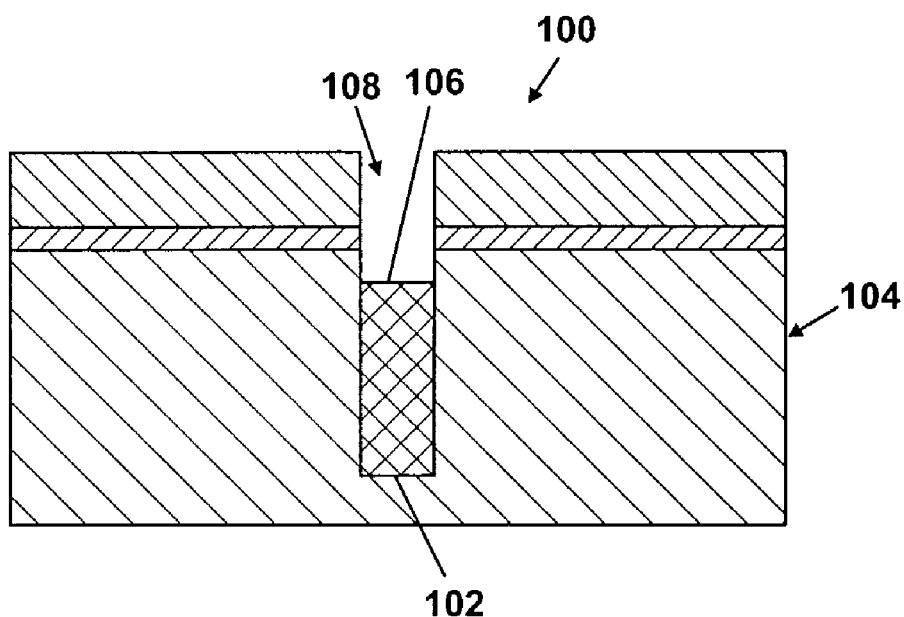
FIG. 1A shows a cross-section of a typical storage node.
Figure 1B:
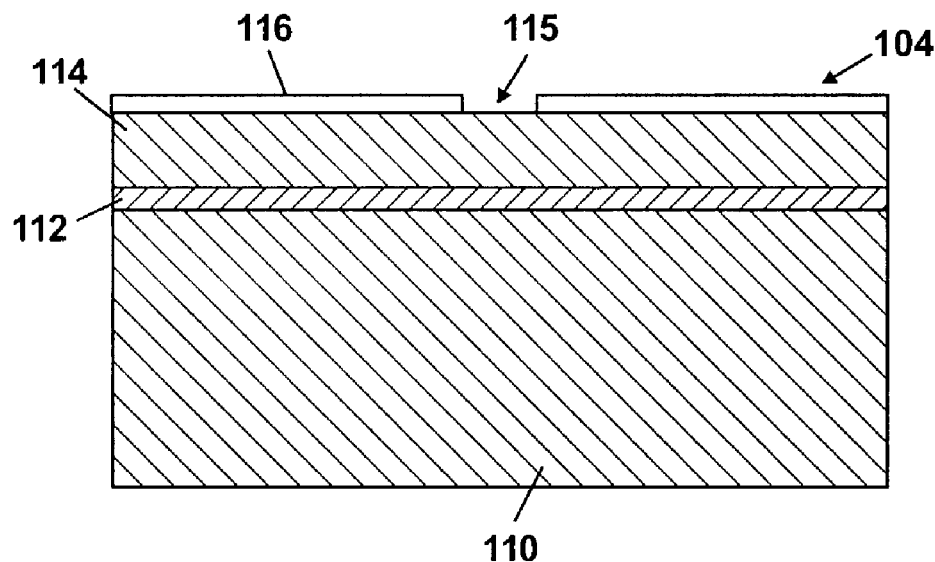
FIG. 1B shows the semiconductor substrate of FIG. 1A prior to forming a trench therein.
Figure 1C:
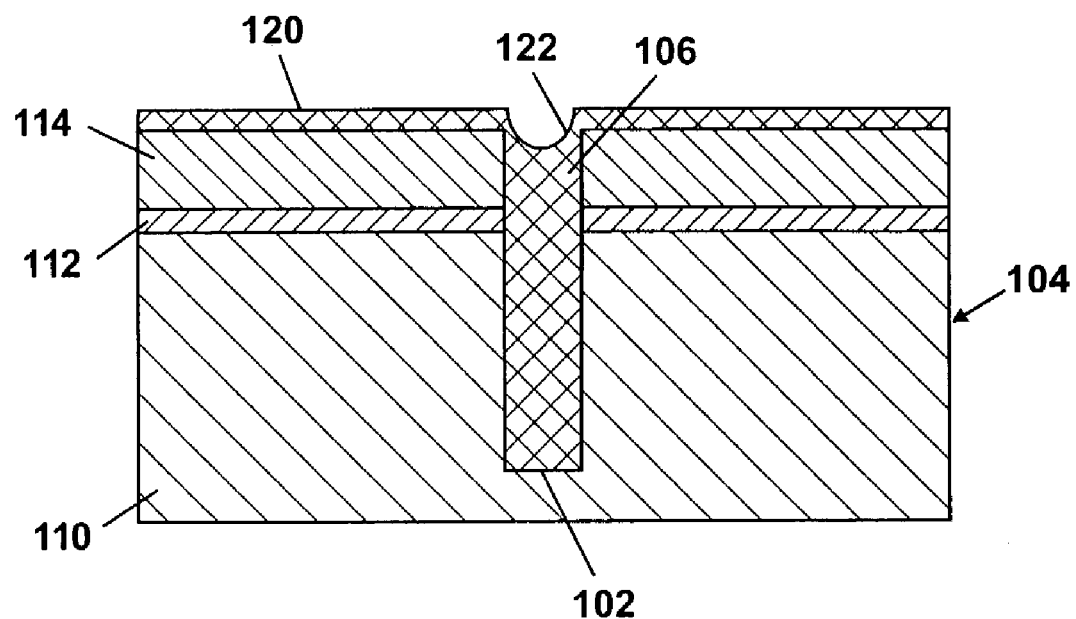
FIG. 1C shows the semiconductor substrate of FIG. 1B after forming a trench therein and filling the trench with polysilicon.
Figure 1D:
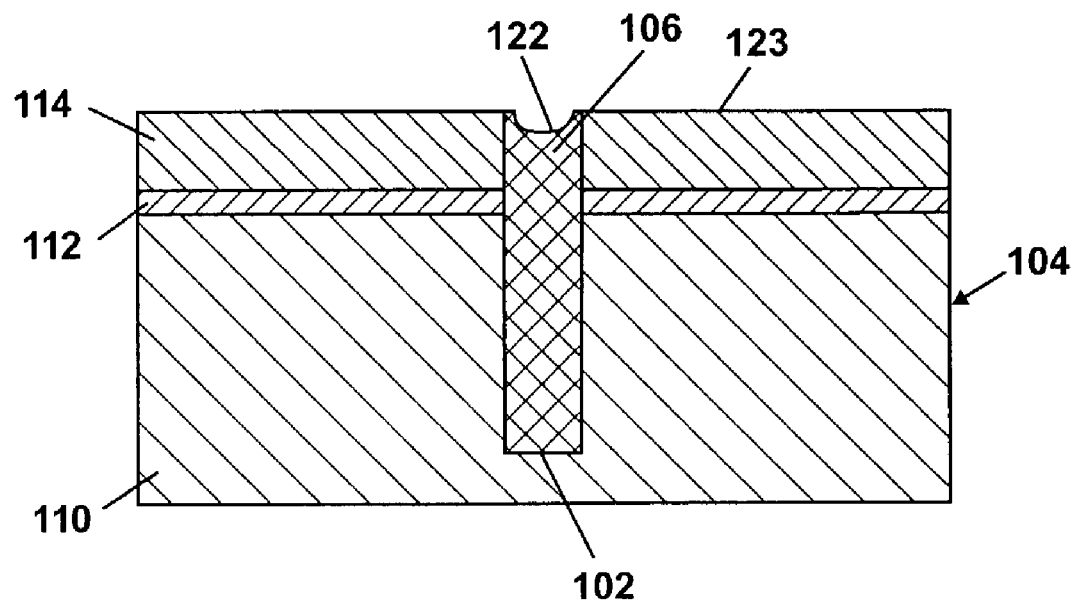
FIG. 1D shows the semiconductor substrate of FIG. 1C after planarizing an overlying blanket of polysilicon.
Figure 1E:
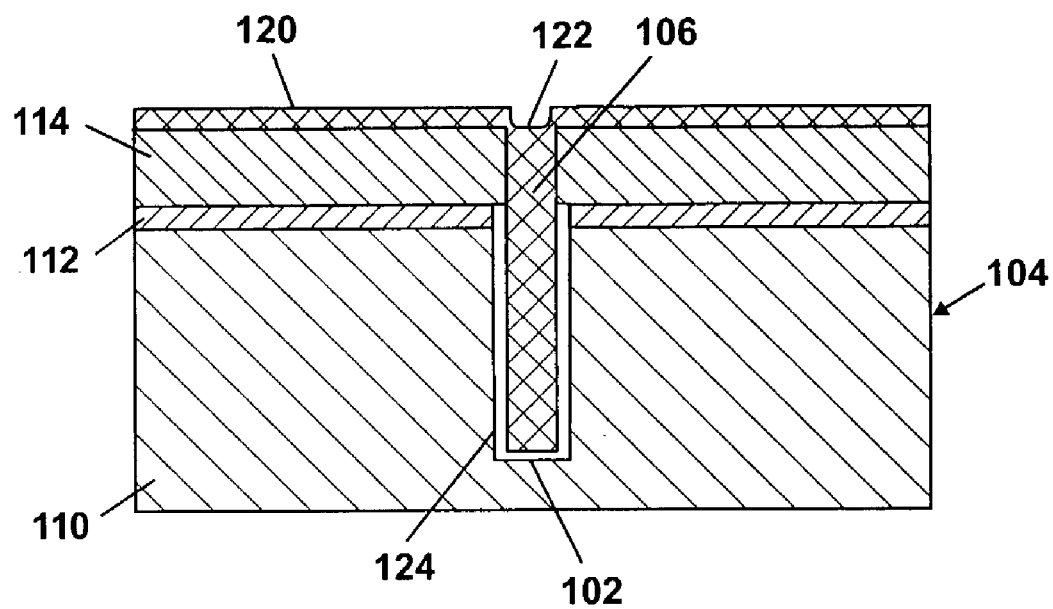
FIG. 1E shows the semiconductor substrate of FIG. 1B after forming a trench therein, lining the trench with a dielectric material, and filling the lined trench with polysilicon.
Figure 1F:
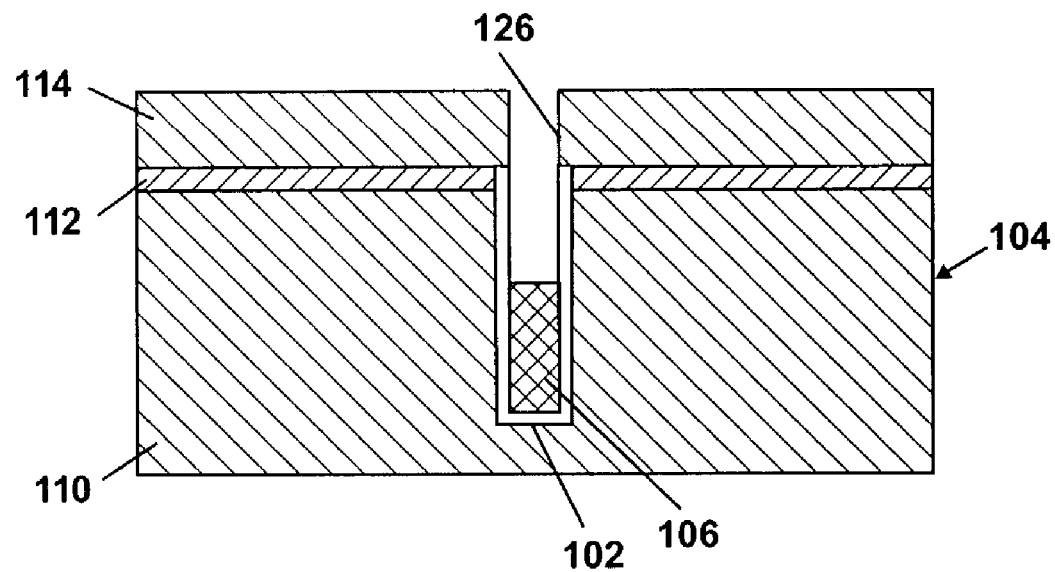
FIG. 1F shows a recess formed in the trench of FIG. 1E.
Figure 1G:
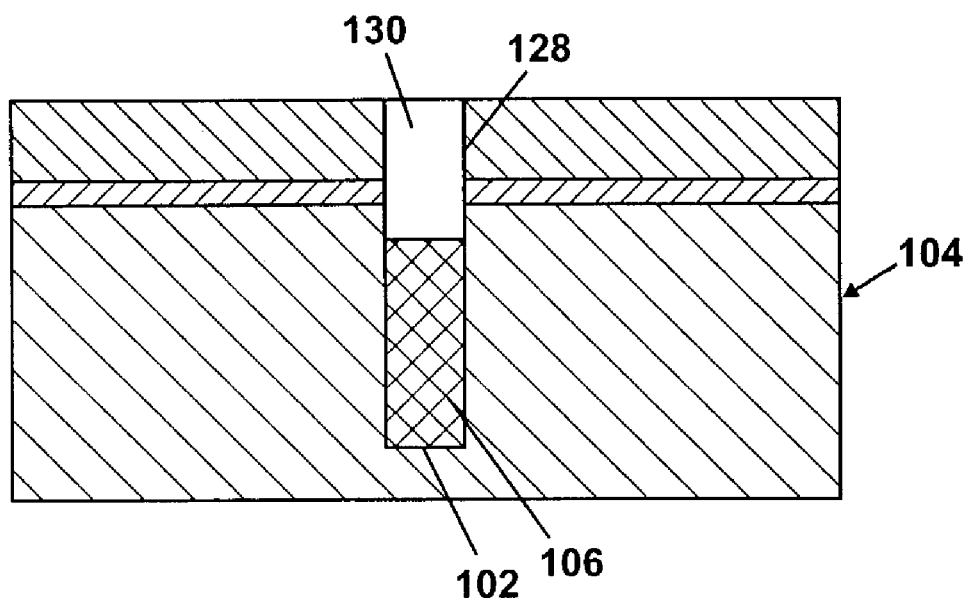
FIG. 1G shows a recess above a column of polysilicon in a trench filled with a dielectric material.
Figure 1H:
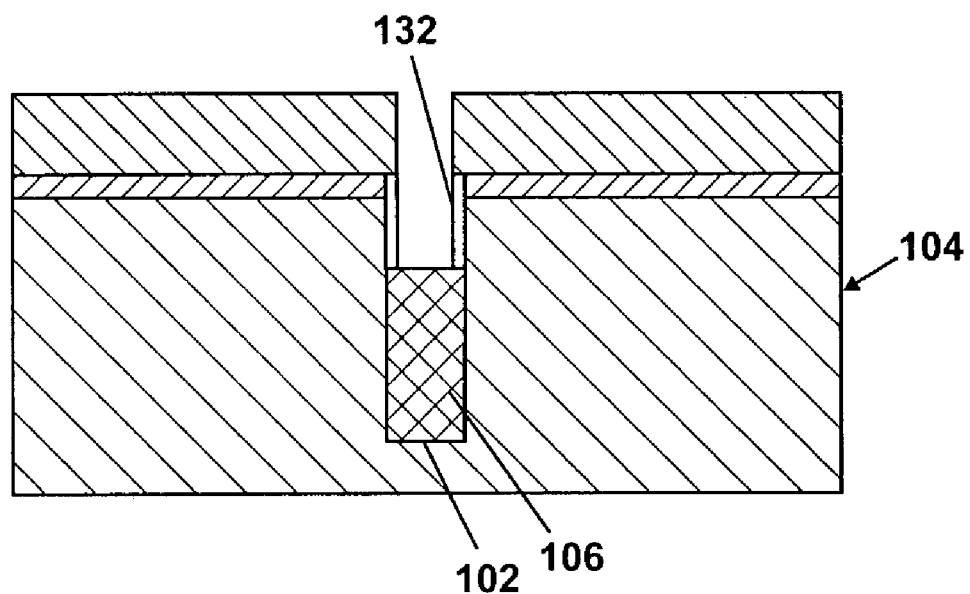
FIG. 1H shows the dielectric material of FIG. 1G partly lining the trench of FIG. 1G.
Figure 2:
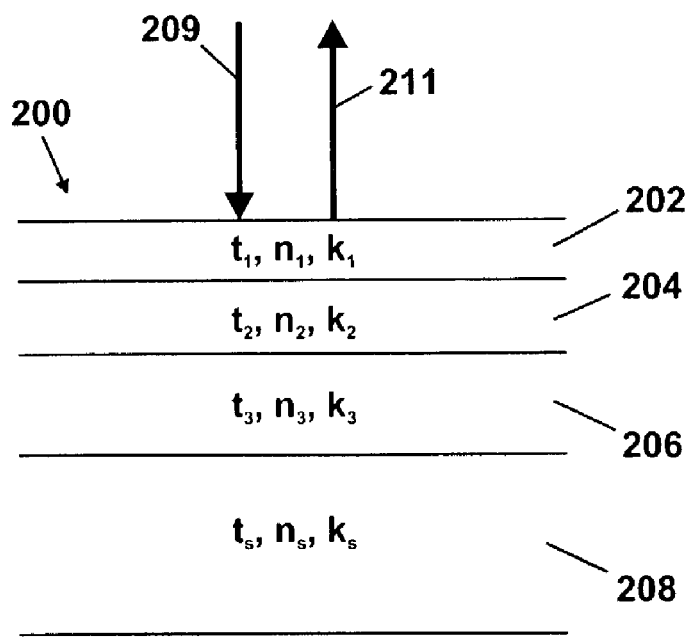
FIG. 2 is a generalized schematic of a thin-film stack.

While not wishing to be bound by theory, the inventors believe herein that a patterned substrate can be divided into n laterally-distinct areas and that each distinct area can be modeled as an isotropic, homogeneous thin-film stack. For illustration purposes, FIG. 2 shows a thin-film stack 200 having a stack of three-film layers 202, 204, 206 on a substrate layer 208. For example, the layer 202 could be made of polysilicon, the layer 204 could be made of silicon nitride, the layer 206 could be made of silicon dioxide, and the layer 208 could be made of silicon. Each of the layers 202, 204, 206, 208 has a thickness (t), a refractive index (n), and an extinction coefficient (k). Reflectance measurements are made by illuminating the thin-film stack 200 at normal incidence with a light beam 209 and collecting the light beam 211 reflected normally from the thin-film stack 200. For normal-incidence reflectometry, the response of an isotropic, homogeneous thin-film stack is polarization-independent. The inventors believe that the patterned substrate 200 can be assumed to have a nominally polarization-independent reflectance, which greatly simplifies the computational aspects of the model.

Figure 3A:
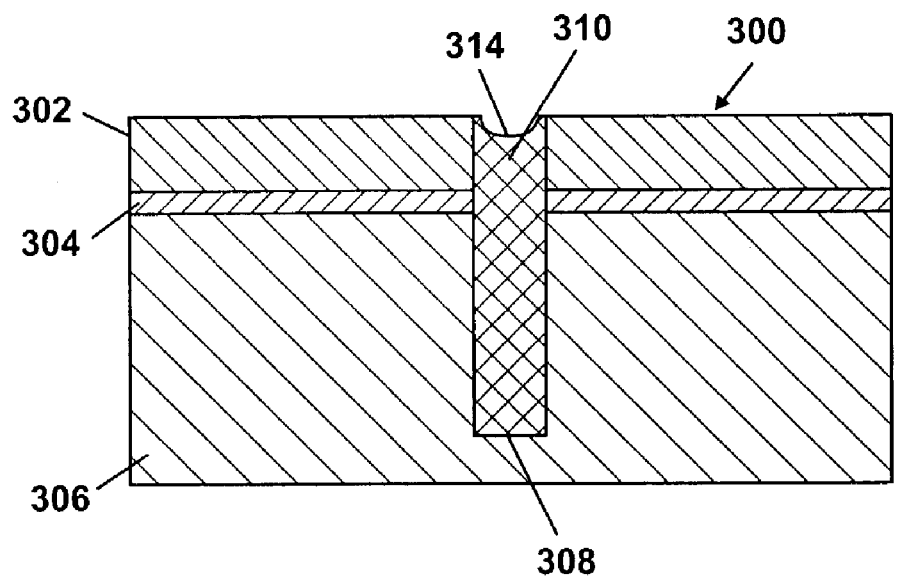
FIG. 3A shows a transverse cross-section of a typical patterned substrate.
Figure 3B:
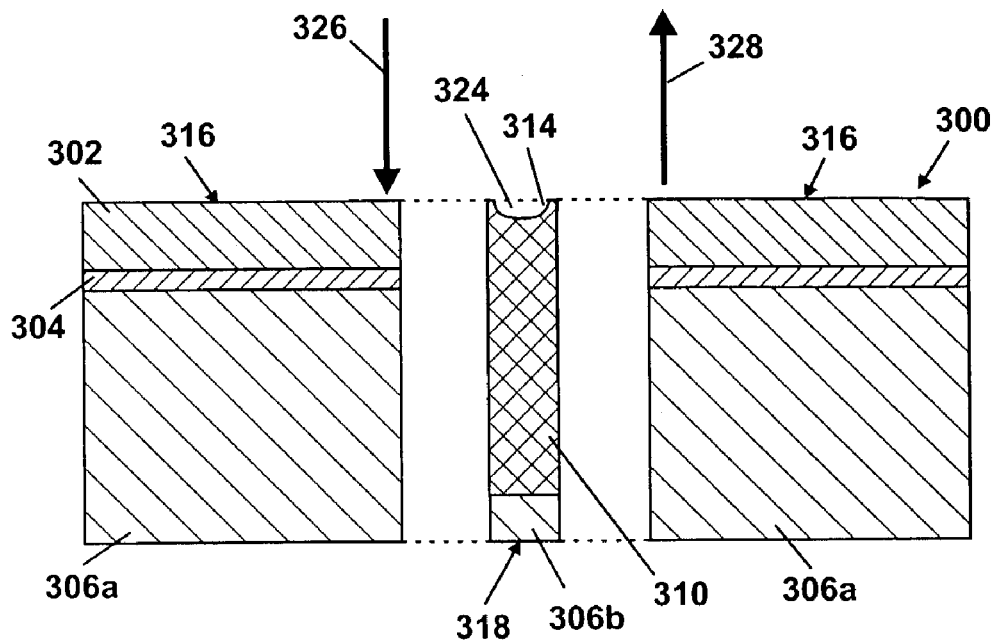
FIG. 3B shows the patterned substrate of FIG. 3A divided into two laterally-distinct areas or thin-film stacks.

The main factors defining lateral distinctness are differences in layers constituting the thin-film stacks and differences in heights of the thin-film stacks. For illustration purposes, FIG. 3A shows a transverse cross-section of a typical patterned substrate 300 having a mask layer 302, an oxide layer 304, and a substrate layer 306. A trench 308 is formed in the substrate 300 and filled with polysilicon 310. A small depression (or dish) 314 is formed at the top of the column of polysilicon 310 in the trench 308 as a consequence of the filling process and planarization processes. FIG. 3B shows the patterned substrate 300 divided into two laterally-distinct areas or thin-film stacks 316, 318. The thin-film stack 316 includes the mask layer 302, the oxide layer 304, and a substrate layer portion 306a. The thin-film stack 318 includes the column of polysilicon 310 and a substrate layer portion 306b.

Figure 3C:
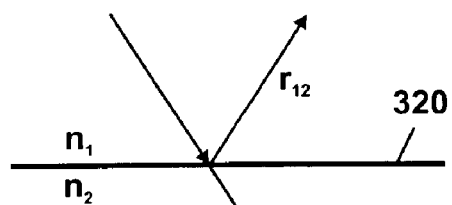
FIG. 3C shows a reflectance model for a layer interface.

The reflectance of the patterned substrate 300 is a combination of the reflected fields from the thin-film stacks 316, 318. The reflected field for a given thin-film stack illuminated by a plane wave of known intensity and polarization can be calculated by setting up and solving a boundary problem or by using Fresnel equations. For example, using Fresnel equations, the reflectance at a layer interface (320 in FIG. 3C) is given by:

$$r_{12} = \frac{n_1 - n_2}{n_1 + n_2} \quad (1)$$

Figure 3D:
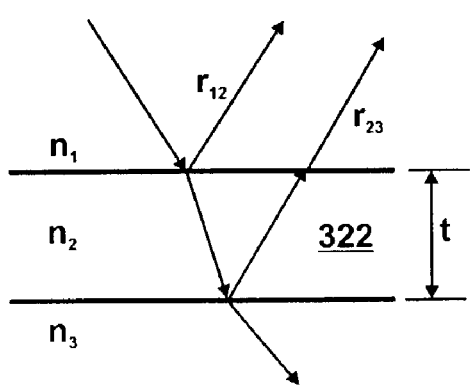
FIG. 3D shows a reflectance model for a single layer.

The reflected field for a single layer (322 in FIG. 3D) is given by:

$$r_{123} = \frac{r_{12} - r_{23}e^{i4\lambda_0 n_2 t}}{1 + r_{12}r_{23}e^{i4\lambda_0 n_2 t}} \quad (2)$$

Returning to FIG. 3B, for the purposes of calculating net reflectance of the patterned substrate 300, the heights of the thin-film stacks 316, 318 should be the same. A layer of air or vacuum 324 is added to the top of the column of polysilicon 310 to compensate for the difference in the heights of the thin-film stacks 316, 318.

The inventors believe herein that given the wide distribution of the lateral extents of features constituting a typical patterned substrate, the reflected fields from the patterned substrate are likely to add coherently over some regions of the pattern and incoherently over some other regions of the pattern. The inventors believe that the relative contributions of the coherently and incoherently combined fields could vary as a function of free-space wavelength, $\lambda_0$, and do not necessarily correspond to the actual area fractions on the patterned substrate. Thus, once the reflected fields from each distinct thin-film stack have been calculated, the net reflectance from a patterned substrate can be calculated as a weighted incoherent sum of reflectances from n different regions constituting the pattern:

$$R = w_1(\lambda_0)|E_1|^2 + w_2(\lambda_0)|E_2|^2 + \ldots + w_n$$

where R is the net reflectance measured, $E_i$ are the individual incoherently adding field terms, and $w_i(\lambda_0)$ are the weighting factors for the incoherently adding terms. The use of $|E_i|^2$ denotes the magnitude of the complex field $E_i$ in the frequency domain notation of electromagnetic field theory.

Each individual incoherently adding term in equation (3) above could be the weighted, coherent sum of fields from k laterally-distinct areas constituting the $i^{th}$ region on the substrate:

$$E_i = \alpha_1(\lambda_0)E_{c1} + \alpha_2(\lambda_0)E_{c2} + \ldots + \alpha_k(\lambda_0)$$

where $\alpha_i(\lambda_0)$ are the weighting factors for coherently adding field terms $E_{ci}$. It should be noted that in equations (3) and (4), a "region" is not the same as a "distinct area."

Figure 3E:
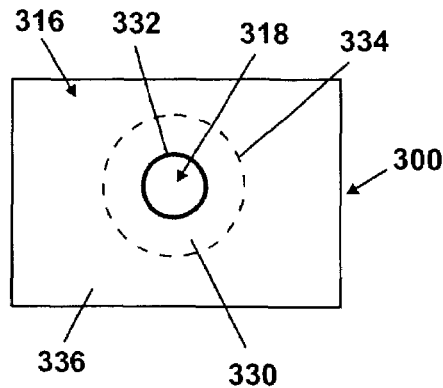
FIG. 3E is a top view of the patterned substrate shown in FIG. 3A.

To further illustrate how the model above works, consider the patterned substrate 300 shown in FIG. 3B. The patterned substrate 300 has been divided into two laterally-distinct areas or thin-film stacks 316, 318. In operation, an incident beam 326 strikes the patterned substrate 300 and is reflected, as shown at 328. FIG. 3E shows a top view of the patterned substrate 300. Let $r_1$ represent the reflected field due to the thin-film stack 316 and $r_2$ represent the reflected field due to the thin-film stack 318. The inventors propose herein that there is a region 330 overlapping the boundary 332 between the thin-film stacks 316, 318, demarcated by imaginary line 334, where the reflection fields $r_1$ and $r_2$ would add coherently because of lateral interference effects. The reflectance from the region 336 outside of the imaginary line 334 is expected to be due to the reflected field from the thin-film stack 316 only.

From equation (3), the net reflectance from the patterned substrate 300 is:

$$R_{300} = w_{336}(\lambda_0)|E_{336}|^2 + w_{330}(\lambda_0)|E_{330}|^2 \quad (5)$$

where $R_{300}$ is the net reflectance from the patterned substrate 300, $E_{330}$, $E_{336}$ are the individual incoherently adding field terms from the regions 330, 336, respectively, and $w_{330}(\lambda_0)$, $w_{336}(\lambda_0)$, are the weighting factors for the incoherently adding terms. From equation (4), $E_{330}$ is:

$$E_{330} = \alpha(\lambda_0)E_{336} + (1-\alpha(\lambda_0))E_{318} \quad (6)$$

It should be noted that $E_{336}$ is $r_1$, $E_{318}$ is $r_2$, and $w_{330}$ can be rewritten as $(1-w_{336})$. Thus, equation (6) can be rewritten as:

$$R_{300} = w_{336}(\lambda_0)|r_1|^2 + (1-w_{336}(\lambda))|\alpha(\lambda_0)r_1 + (1-a(\lambda_0))r_2|^2$$

Equations (3) and (4) provide a simplified model wherein reflectance from a patterned substrate can be parameterized with respect to several quantities of interest, such as mask layer thickness and starting etch depth. In one embodiment, the invention uses normal incidence reflectometry as a technique for measuring reflectance, meaning the patterned substrate is illuminated by a beam incident normal to the substrate and only the light reflected normal to the substrate is collected, i.e., only specularly reflected light is collected. However, because a range of orientations can be seen in any pattern, not all of the light striking the pattern will reflect at normal incidence. There will be non-specular reflection due to, for example, the depression (314 in FIG. 3A). Reflection losses due to such non-specular reflection should not be ignored. In an embodiment of the invention, a scattering loss factor is applied to parts of the adding terms in equation (3) or to the entire reflectance in equation (3). The scattering loss factor could be a function of $\lambda_0$.

Figure 4A:
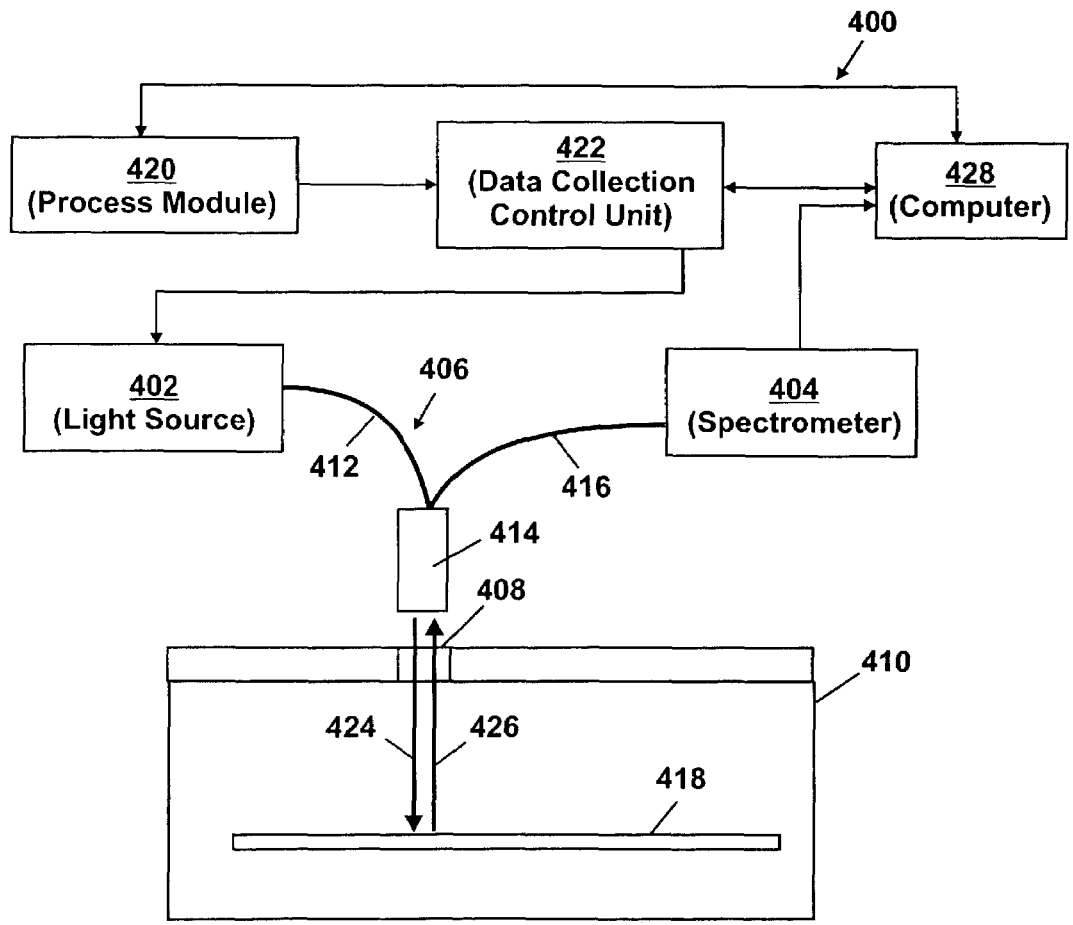
FIG. 4A shows a process setup according to an embodiment of an invention.

FIG. 4A is a simplified schematic of a system 400 for estimating in-situ incoming material variations according to an embodiment of the invention. The system 400 includes a light source 402 for generating a light beam, a spectrometer 404 for detecting and analyzing a light beam, and an optical system 406 for transporting light to and from a port 408 at the top of a process chamber 410. For example, the optical system 406 could include an optical fiber 412 that transports light from the light source 402 to a collimator 414, where the collimator 414 is mounted above the port 408, and an optical fiber 416 that transports light from the collimator 414 to the spectrometer 404. A semiconductor substrate 418 is mounted inside the process chamber 410. To avoid obscuring the invention, the details of the processing equipment are not shown. However, it will be obvious to one of ordinary skill in the art what equipment is needed to perform the etching. For example, if the recess is to be formed via plasma etching, the substrate 418 would be mounted on a chuck (not shown) in the process chamber 410, and the appropriate equipment for generating the plasma would be provided.

In operation, a process module 420 that controls processing of the semiconductor substrate 418 sends a signal to a data collection unit 422 to trigger operation of the light source 402. When the light source 402 is triggered, it generates a light beam, which is transported through the optical fiber 412 to the collimator 414. The operating wavelength band of the light source 402 is selected to be in the region where sensitivity to the parameters of interest is heightened. Generally speaking, a broader range is more useful. In one example, the wavelength range of the light source is 190 to 1000 nm. The light beam 424 leaves the collimator 414, passes through the port 408, and strikes the substrate 418 at normal incidence. The collimator 414 collects the light beam 426 reflected normally from the substrate 418 at normal incidence. The reflected light beam 426 travels to the spectrometer 404 through the optical fiber 416. The spectrometer 404 analyzes the reflected light beam 426 and sends data representative of the reflectance spectrum of the substrate 418 to a computer 428 for further analysis.

The computer 428 includes a model for calculating reflectance of a patterned substrate, such as substrate 418, and a routine that searches for a set of parameterized parameters that provides an optimal match between the modeled reflectance spectrum and the measured reflectance spectrum received from the spectrometer 404. In one embodiment, the search routine is a non-linear regression routine. However, other types of search routines, such as multivariate regression analysis or neutral net matching, can also be used. A model for calculating reflectance of a patterned substrate has been described above. The set of parameters obtained can be mapped to several key quantities of interest, such as mask layer thickness and starting etch depth. The quantities of interest can then be used to determine an endpoint in the recess etch process, as will be further described below.

Figure 4B:
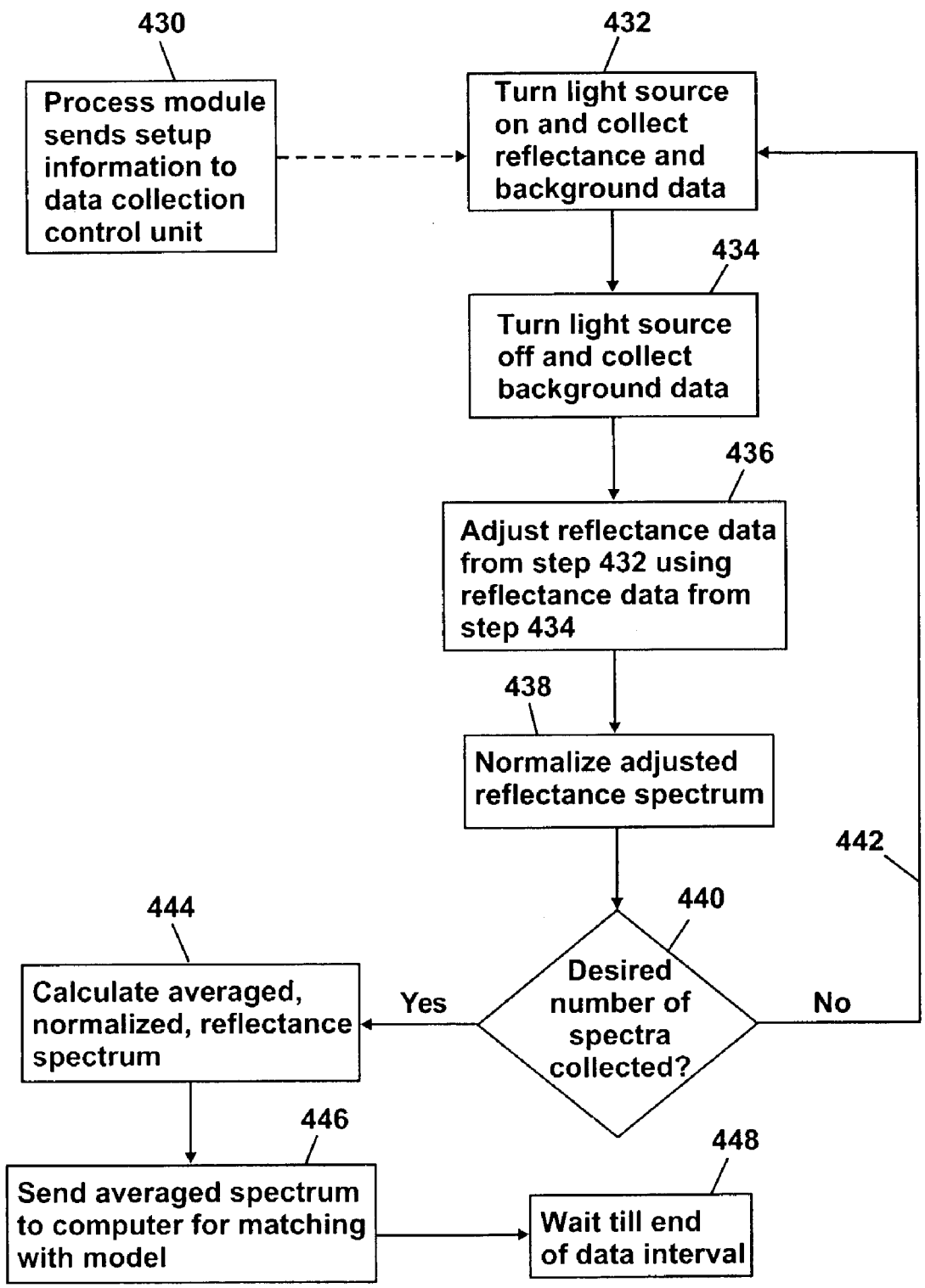
FIG. 4B is an overview of a process for collecting normal incidence reflectance data according to one embodiment of the invention.

FIG. 4B is an overview of a process for collecting normal reflectance data from a substrate according to an embodiment of the invention. One objective is to improve a high-quality reflectance signal even in the presence of significant background light levels such as the emission from a luminous plasma. At the start of the process, the process module (420 in FIG. 4A) informs the data collection control unit (422 in FIG. 4A) about how the reflectance data should be collected and calibrated (430). For example, the process module tells the data collection control unit the number of reflectance spectra and the length of time for which the spectra should be collected. The process module also gives the data collection control unit a baseline reflectance spectrum, typically a bare silicon reflectance spectrum, for calibration of the measured reflectance spectra. The bare silicon reflectance spectrum is collected prior to processing the substrate. When the data control collection control unit receives instruction to start collecting data, the light source (402 in FIG. 4A) is turned on to generate a light beam, which is directed to strike the substrate, and the spectrometer (404 in FIG. 4A) collects reflectance data from the substrate (432). Then, the light source is turned off and the reflectance data is collected again (434). When the light source is turned off, the data collected by the spectrometer is due to background sources, such as from plasma emissions, and detector noise. The next step is to subtract the reflectance data obtained in step 434 from the reflectance obtained in step 432 to remove the contribution of the background sources.

The corrected reflectance spectrum is normalized by a baseline spectrum (438). Then, the system checks if the desired number of reflectance spectra has been collected (440). If the desired number of reflectance spectra has not been collected, the system returns to step 432 and starts collecting data for another reflectance spectrum (442). If the desired number of reflectance spectra has been collected, the system computes an average of the collected reflectance spectra to obtain an averaged, normalized, reflectance spectrum (444). The averaged reflectance spectrum is sent to the computer (428 in FIG. 4A) for matching with the model of the substrate (446). After sending the averaged reflectance spectrum to the computer, the system waits for the end of the specified length of time, after which it terminates (448).

Figure 4C:
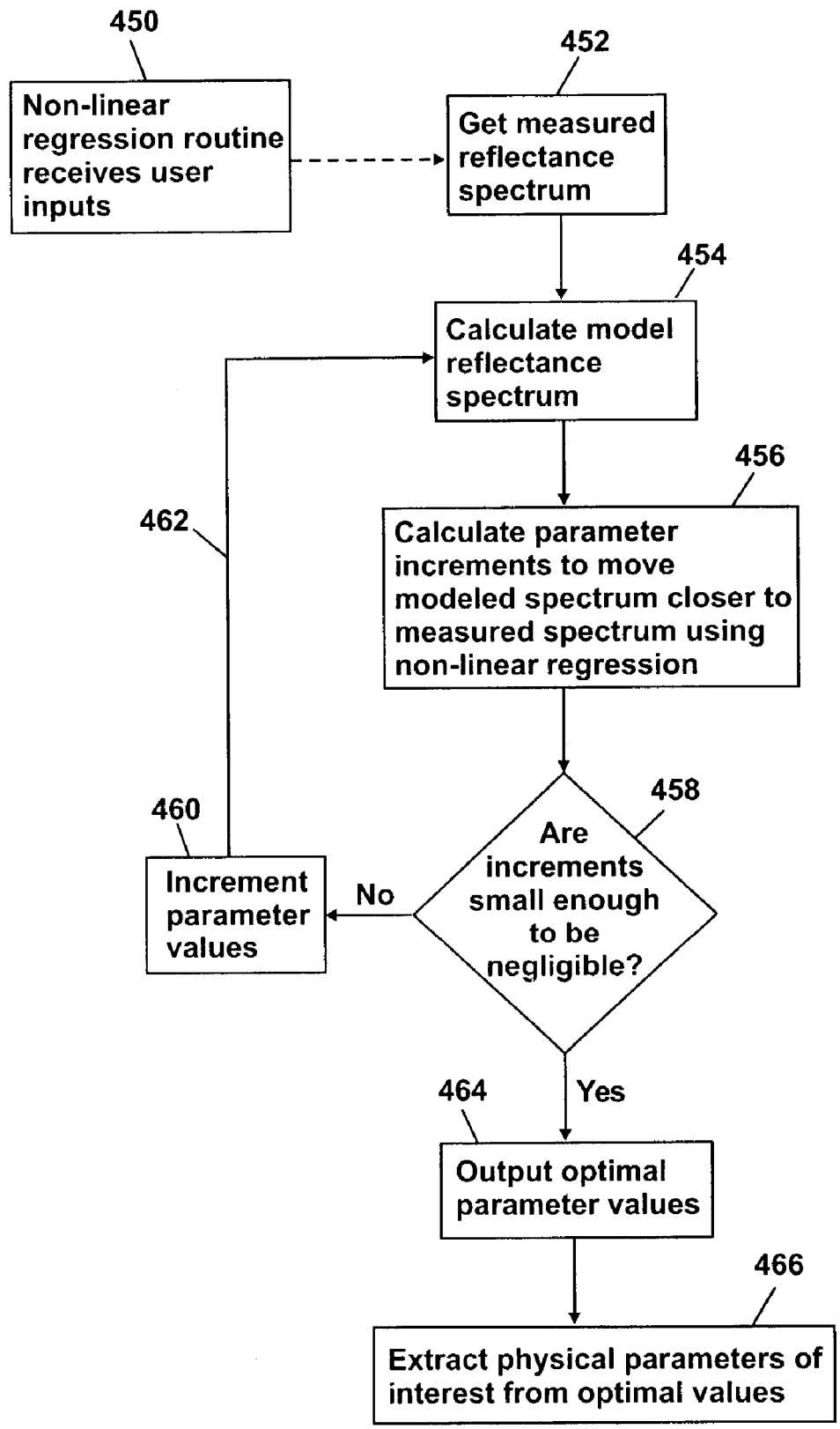
FIG. 4C is an overview of a process for matching measured reflectance spectrum to modeled reflectance spectrum according to one embodiment of the invention.

FIG. 4C is an overview of a process for determining physical parameters of interest using a non-linear regression scheme. One objective is to quickly reach a converged set of parameter values by incrementally stepping the parameter values in the appropriate direction through the parameter space till the solution is reached. Prior to start of the non-linear regression analysis, the non-linear routine receives user inputs (450). The user inputs include initial guesses for a set of parameters to be determined by matching the reflectance spectrum to the modeled spectrum. The non-linear regression routine then obtains the averaged measured reflectance spectrum (452). Next, the modeled reflectance spectrum is calculated using equations (3) and (4) and the initial guesses (454). Then, the non-linear regression routine is used to calculate increments to the parameters in equations (3) and (4) to move closer to the best match between the measured reflectance spectrum and the modeled reflectance spectrum (456). The parameters in equations (3) and (4) are the reflected fields, the weighting factors w, and the coupling factors α, which can be functions of the free-space wavelength, $\lambda_o$.

The system checks whether the increments calculated in step 456 are small enough to be negligible (458). If the increments are not small enough to be negligible, the system increments the values of the parameters (460) and returns to step 454 to recalculate the modeled reflectance spectrum using the new parameter values (462). If the increments are small enough to be negligible, the system outputs the optimal parameter values (464). The physical parameters of interest are then extracted from the optimal parameter values (466). Although not stated previously, the user inputs received in step 450 also include information about how to subdivide the substrate into laterally-distinct areas or thin-film stacks. The user inputs also include optical properties of each thin-film stack so that the reflected fields of each thin-film stack can be calculated, as previously described.

In one embodiment, the invention uses a modified version of a non-linear regression technique called the Levenberg-Marquardt Compromise to quickly and accurately locate optimal values of key parameter values starting from the initial guesses of the parameter values. Although, the Levenberg-Marquardt Compromise technique is a preferred technique, other techniques, such as multivariate regression analysis and neural net approaches, may also be employed to extract parameters of interest.

Figure 4D:
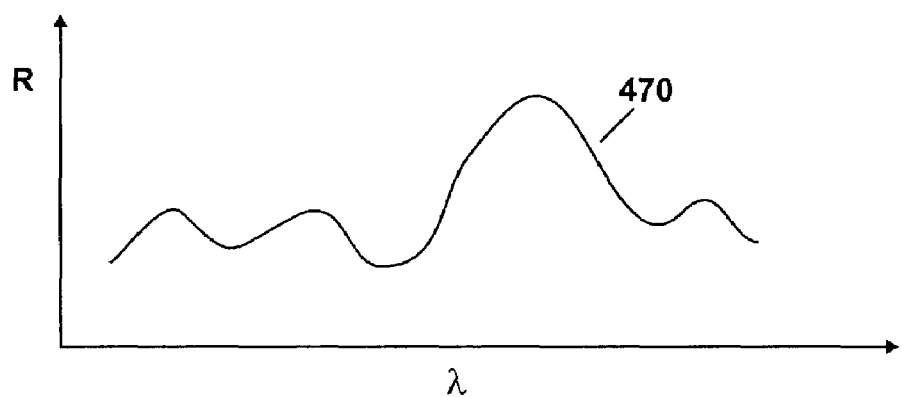
FIG. 4D is a schematic depicting a measured reflectance spectrum.
Figure 4E:
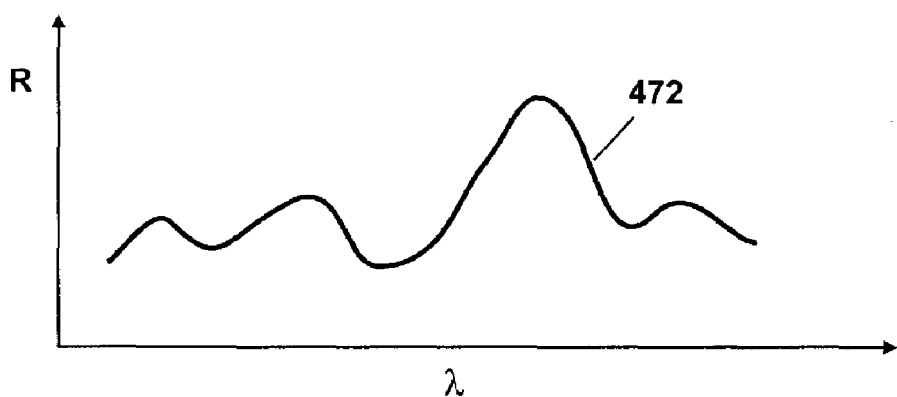
FIG. 4E is a schematic depicting a modeled reflectance spectrum.
Figure 4F:
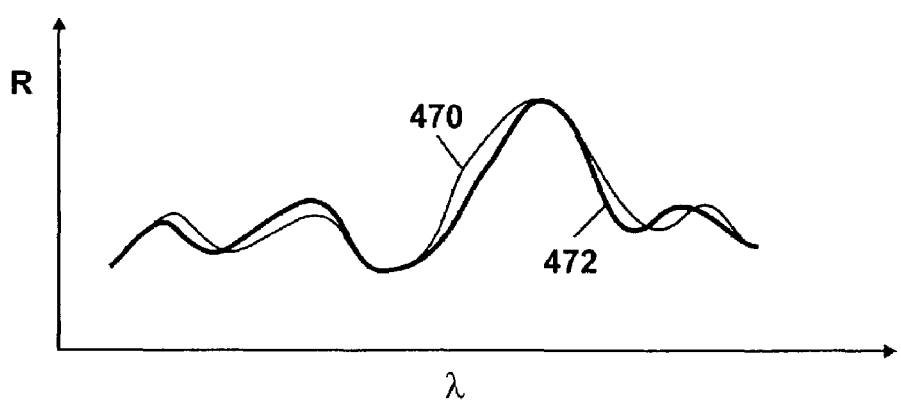
FIG. 4F compares the measured reflectance shown in FIG. 4D to the modeled reflectance spectrum shown in FIG. 4E.

To illustrate how the non-linear regression works, FIG. 4D shows a measured reflectance spectrum 470, and FIG. 4E shows a modeled reflectance spectrum 472 computed using initial guesses from user inputs. The first step in the linear regression routine is to calculate a least squares difference error metric between the two reflectance spectra 470, 472. FIG. 4F shows the measured reflectance spectrum 470 superimposed on the modeled reflectance spectrum 472. The least squares difference is computed by taking several points across the wavelength range, calculating the vertical difference between the spectra 470, 472 at each point, and summing the square of the differences at all the points. The least squares difference error metric is then used to determine the increments for the parameter values.

So far, the description of the non-linear regression analysis above is standard. Now, what happens in many cases is that a lot of the parameters that are not of interest cause significant changes in the entire modeled spectrum while the parameters of interest cause changes in small regions of the modeled spectrum. To allow the parameter values of interest to be located quickly and accurately, the differences in the regions of the spectrum where the parameters of interest are expected to make a difference are amplified by a factor, e.g., $(1+\gamma_1)$, prior to summing the square of the differences at all the points. Thus, the least squares difference error is larger if the differences in the region of interest are larger. A constant or weighting factor may also be applied to the amplification factor to further bias the least squares difference error metric.

Figure 5A:
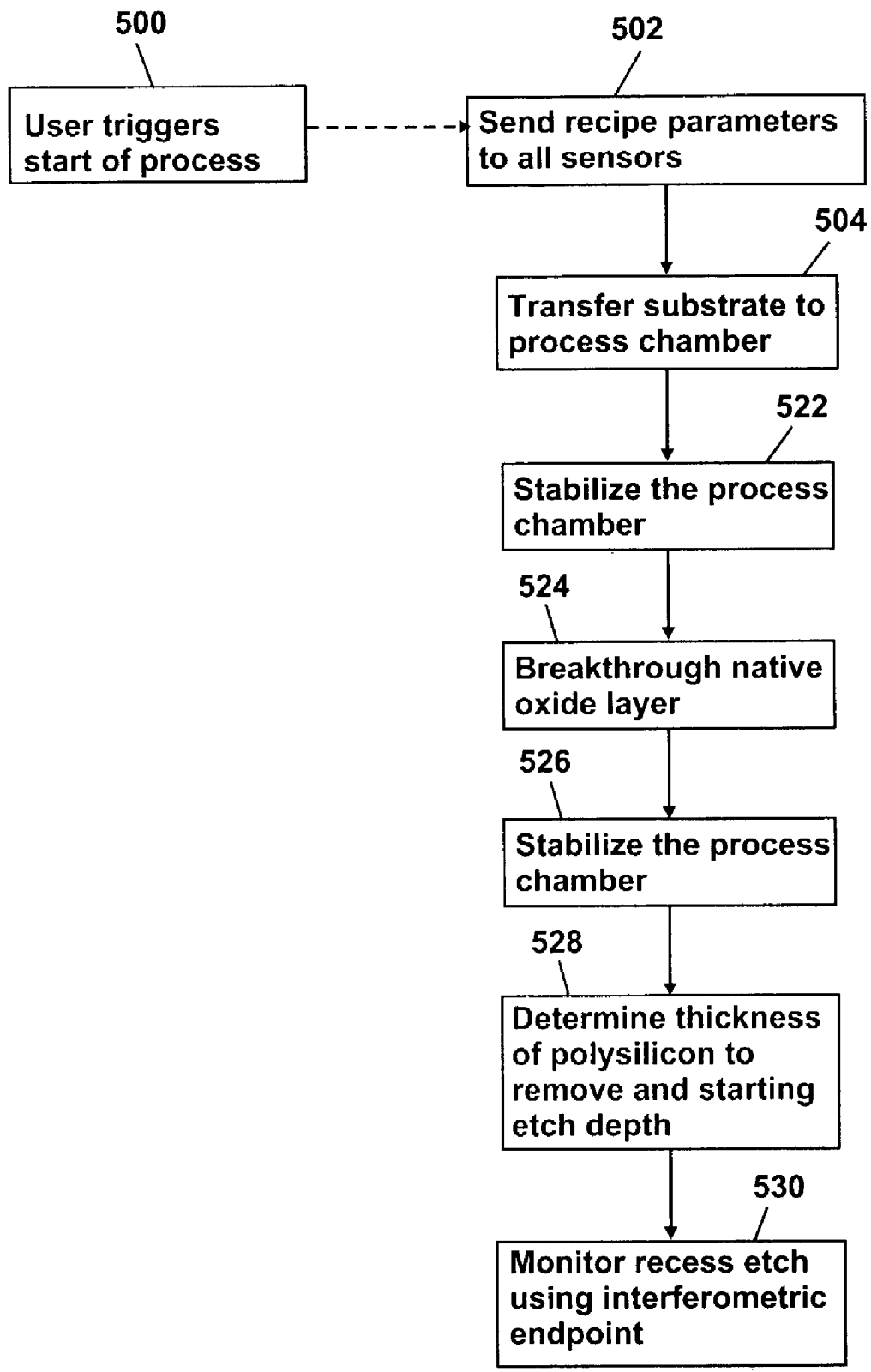
FIG. 5A is an overview of a process for detecting an endpoint in a recess etch process according to one embodiment of the invention.
Figure 5B:
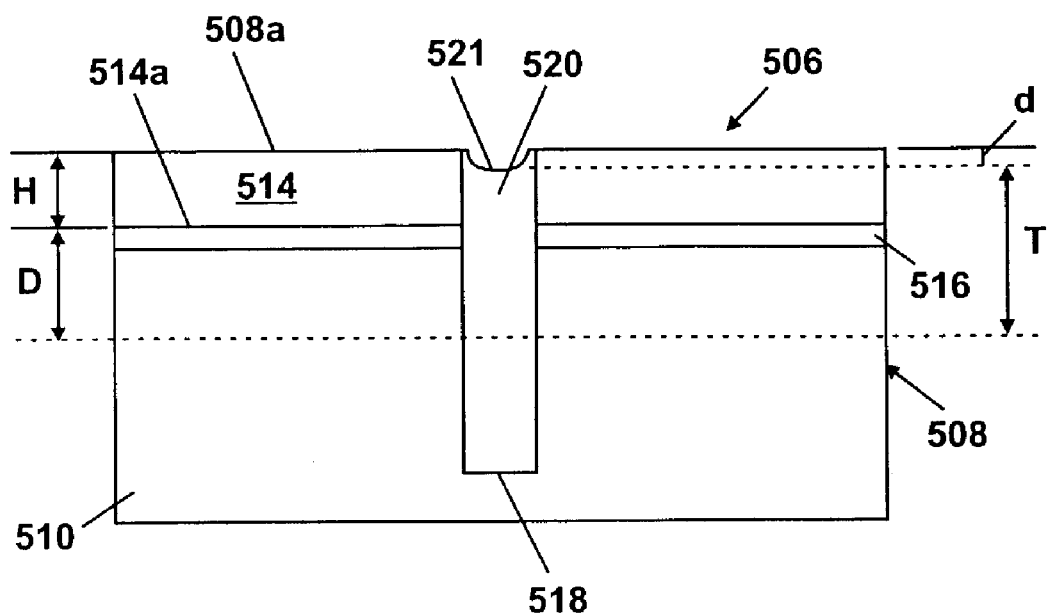
FIG. 5B is a pre-etch model according to one embodiment of the invention.

FIG. 5A is an overview of a process for detecting an endpoint in a recess etch process according to an embodiment of the invention. The start of the process is triggered by a user (500). When the process starts, the process module (420 in FIG. 4A) sends the appropriate process recipe parameters to all the sensors (502). The process recipe parameters could include, for example, the target recess depth relative to a reference point on the substrate, such as the bottom of a mask layer. The semiconductor substrate of interest is then transferred to the process chamber (410 in FIG. 4A), or may already be in the process chamber (504). For illustration purposes, FIG. 5B shows a pre-etch model 506 assumed in this process. The pre-etch model 506 includes a patterned semiconductor substrate 508 having a substrate layer 510. One or more layers, e.g., a mask layer 514 and an oxide layer 516, are formed on the substrate layer 510. A trench 518 is formed in the substrate 508 and filled with a column of polysilicon 520. In this model, all of a polysilicon layer (not shown) previously overlying the mask layer 514 has been planarized. However, this does not have to always be the case, i.e., an amount of polysilicon may remain on the mask layer 514 prior to recess etching.

Returning to FIG. 5A, after mounting the semiconductor substrate in the process chamber (410 in FIG. 4A), gas flow into the process chamber is stabilized (522). A breakthrough process is then performed to remove any native oxide buildup on the semiconductor substrate as a result of exposing silicon to air (524). The breakthrough process can be a timed-etch process and should typically last for just a few seconds. It should be noted that the breakthrough process can result in loss of material from the top of the semiconductor substrate, which may need to be compensated for at a later stage. After the breakthrough process, gas flow into the process chamber is again stabilized (526). The next step is to estimate in-situ the incoming material variations (528). This step would include estimating thickness of one or more layers, such as a mask layer, as well as the starting etch depth, e.g., depth of depression above the column of polysilicon in the trench. This step could be executed during or after the stabilization step 526. Performing the estimation step 528 concurrently with the stabilization step 526 would save substrate processing time.

In the pre-etch model 506 shown in FIG. 5B, the bottom 514a of the mask layer 514 is used as a reference point. It should be noted that other points on the substrate 508, e.g., the top of the substrate layer 510, can also be used as a reference point. The desired recess depth (D) measured from the reference point 514a would be a known quantity. The first vertical dimension of interest (H) would then be the vertical distance from the top 508a of the substrate 508 to the reference point 514a, which in this case corresponds to the thickness of the mask layer 514. The second vertical dimension of interest (d) would be the vertical distance from the top 508a of the substrate 508 to the top of the polysilicon column 520, i.e., the depth of the depression 521 at the top of the polysilicon column 520. Once the dimensions H and d are known, the thickness of material (T) to be removed from the top of the polysilicon column 520 can be determined, i.e., $T=H+D-d$. Returning to FIG. 5A, the physical parameters of interest, e.g., H and d, can be estimated in step 528 using the broadband reflectometry method described above, i.e., by determining a set of parameters that provide a close match between a measured reflectance spectrum of the substrate and a modeled reflectance spectrum of the substrate and extracting the desired dimensions from the set of parameters.

Once the thickness of material to be removed from the polysilicon column and the starting etch depth are known, the recess etch process can be started. Any suitable etching method, such as plasma etching, can be used to remove material from the polysilicon column. In one embodiment, an interferometric endpoint detection method is used to control the etching of the polysilicon column (530). The interferometric endpoint detection method involves counting the number of fringes evolved during the etch. When a predetermined number of fringes corresponding to the thickness of material to be removed has been counted, the recess etching process is stopped.

The interferometric approach involves directing a light beam to the polysilicon column. The light beam is partially reflected from the surface of the polysilicon column, partially transmitted through the polysilicon column, and reflected by the underlying substrate layer, as the polysilicon column is etched. The reflected signals combine constructively or destructively to produce a periodic interference fringe. The maxima and minima of the interference fringe depends on the path length of the light beam through the thickness of the polysilicon column being processed. During etching, the observed periodic maxima and minima of a measured interference fringe is correlated to a calculated reduction in the thickness of the polysilicon column to estimate an endpoint in the process. The interferometric approach can be used for monitoring the recess etch process because the absolute thickness of material to remove from the polysilicon column is known, i.e., from the broadband reflectometry scheme described above.

Although an interferometric approach is discussed above as a preferred method for monitoring recess etching after accurately determining the initial thickness of the polysilicon column, it should be clear that other techniques may also be used. For example, the broadband reflectometry scheme described above can be used in-situ to determine the absolute thickness of the polysilicon as it is etched down to form the recess. This would involve continuously measuring a net reflectance of the substrate, finding a set of parameters that provide an optimal match between the measured net reflectance spectrum and a modeled reflectance spectrum of the substrate, and extracting the thickness of the polysilicon column from the set of parameters. When the desired thickness of the polysilicon column has been reached, the recess etch process can be stopped. A timed-etch process may also be used. That is, the time required to etch down a predetermined amount of material from the polysilicon column can be determined. The polysilicon column can then be etched for the predetermined time.

Figure 6A:
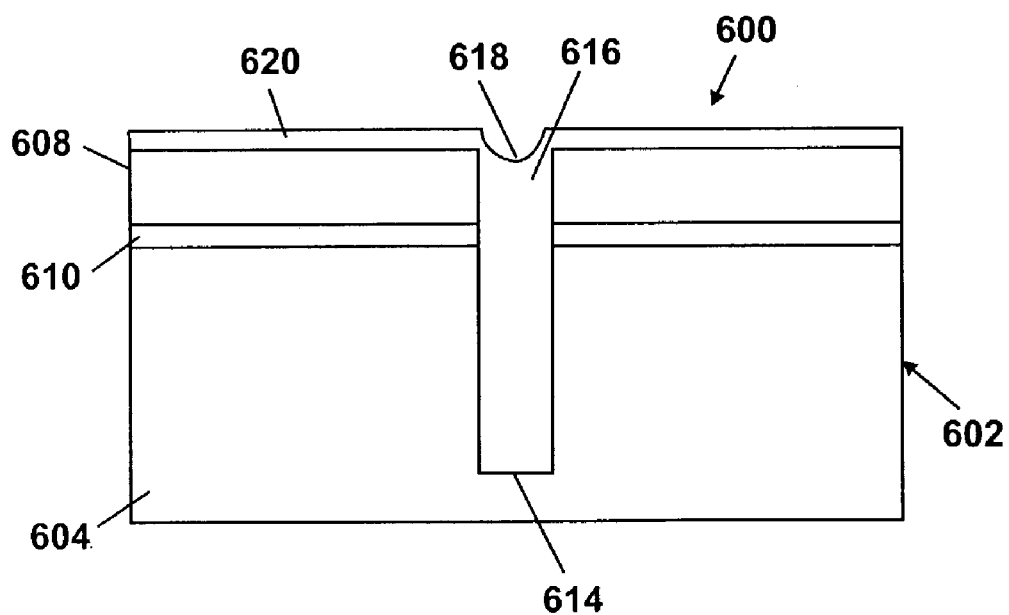
FIG. 6A is a pre-etch model according to another embodiment of the invention.

Various modifications can be made to the process sequence described in FIG. 5A. For example, the process sequence in FIG. 5A assumes a pre-etch model (506 in FIG. 5B) wherein a polysilicon layer overlying, for example, a mask layer has already been planarized using, for example, a chemical-mechanical polishing process. In another embodiment of the invention, the process sequence may include a planarization step. For example, FIG. 6A shows a pre-etch model 600 that includes a patterned semiconductor substrate 602 having a substrate layer 604. One or more layers, e.g., a mask layer 608 and an oxide layer 610, are formed on the substrate layer 604. A trench 614 is formed in the substrate 602 and filled with a column of polysilicon 616. A depression 618 is formed at the top of the column of polysilicon 616 as a consequence of the filling process. A layer of polysilicon 620 is also formed on the mask layer 608 during the filling process.

Figure 6B:
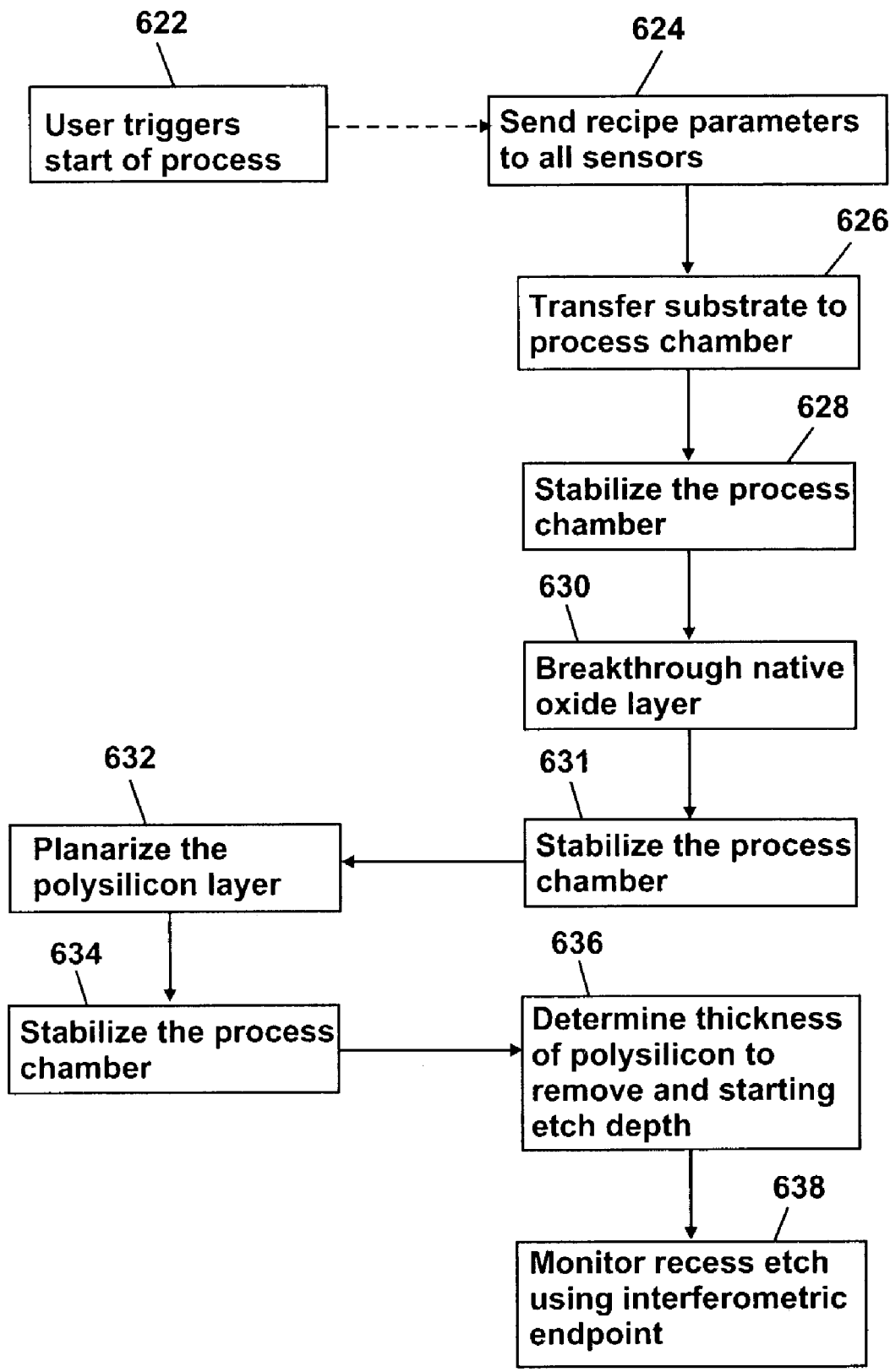
FIG. 6B is an overview of a process for detecting an endpoint in a recess etch process according to another embodiment of the invention.

FIG. 6B is an overview of a process for detecting an endpoint in a recess etch process assuming the pre-etch model (600 in FIG. 6A). The start of the process is triggered by a user (622). When the process starts, the process module (420 in FIG. 4) sends the appropriate process recipe parameters to all the sensors (624). The process recipe parameters could include, for example, the target recess depth measured from a reference point on the substrate, such as the bottom of the mask layer. The semiconductor substrate of interest is then transferred to the process chamber (410 in FIG. 4), or may already be in the process chamber (626). After mounting the semiconductor substrate in the process chamber, gas flow into the process chamber is stabilized (628). A breakthrough process is then performed to remove any native oxide buildup on the semiconductor substrate as a result of exposing silicon to air (630). After the breakthrough process, gas flow into the process chamber is again stabilized (631). The layer of polysilicon (620 in FIG. 6A) is then planarized using, for example, plasma etching (632). All or only a portion of the layer of polysilicon may be removed. If all of the polysilicon layer is removed, there may be some loss of material from the mask layer (608 in FIG. 6A) underlying the polysilicon layer, which may need to be compensated for at a later stage. An interferometric approach or other suitable method can be used to determine when to end the planarization process.

After the planarization step, gas flow into the process chamber (410 in FIG. 4) is again stabilized (634). The next step is to estimate in-situ incoming material variations (636), i.e., estimate the vertical dimension from the top surface of the substrate to a reference point on the substrate, such as the bottom of the mask layer, and the vertical dimension from the top surface of the substrate to the top of the polysilicon column, i.e., starting etch depth. This estimate will factor in any material loss as a result of the planarization and breakthrough processes. Estimation of the incoming material variations, i.e., step 636, can be done concurrently with or after the stabilization step 634. In a manner similar to the one described above for step 528 in FIG. 5A, the physical parameters of interest are determined in step 636. These physical parameters are then used to drive the recess etching process (638), in a manner similar to one described for step 530 in FIG. 5A.

The invention provides one or more advantages. For example, the method of the invention can be used to detect an endpoint while forming a recess in a column of material in a trench. The method is applicable to any of the recess structures described in the background section as well as other recess structures not illustrated. Basically, the inventors recognize that there will be material variations from one substrate to another which will affect the thickness of material to remove from the column of material in the trench to achieve a desired recess depth. The general idea then is to determine the absolute thickness of material to remove prior to starting the etching process and then use this thickness to drive the etching process. The invention uses a broadband reflectometry method, including a robust model of the substrate and a biased non-linear regression technique, to accurately estimate the thickness of material to be removed via etching. With this accurate estimate, an interferometric approach, or other suitable method, can then be used to determine when to end the recess etch process.

While the invention has been described in terms of several preferred embodiments, there are alterations, permutations, and equivalents which fall within the scope of this invention. For example, the process sequences illustrated in FIGS. 5A and 6B are just examples based on the pre-etch models shown in FIGS. 5B and 6A, respectively. The process sequence will generally need to be adjusted based on the pre-etch state of the substrate and the desired recess structure. As previously mentioned, the basic idea is to get an accurate estimate of the thickness of material to be removed and the starting etch depth prior to etching. These parameters can then be used to drive the etching process.

Further, in estimating the incoming material variations, other techniques besides the Levenberg-Marquardt Compromise can be used to match the measured reflectance spectrum to the modeled reflectance spectrum of the substrate. For example, multivariate regression analysis and neural net match approaches can be used.

Further, monitoring of the recess etch process is not limited to an interferometric approach. A timed-etch process could be used, for example.

Further, the invention is not limited to making trench capacitors. For example, the invention can be used in monitoring recess etch processes used in forming chip interconnects.

What is intended therefore is that the following appended claims be interpreted as including all such alterations, permutations, and equivalents as fall within the true spirit and scope of the invention.

What is claimed is:

1. A method of controlling a recess etch process, comprising:
    for a multilayered substrate having a trench therein and a column of material deposited in the trench, determining a first dimension from a surface of the substrate to a reference point in the substrate by:
        obtaining a measured net reflectance spectrum of at least a portion of the substrate including the trench;
        computing a modeled net reflectance spectrum of the portion of the substrate as a weighted incoherent sum of reflectances from $n \geqq 1$ different regions constituting the portion of the substrate;
        determining a set of parameters that provides a close match between the measured net reflectance spectrum and the modeled net reflectance spectrum; and
        extracting the first dimension from the set of parameters;
    computing an endpoint of the recess etch process as a function of the first dimension and a desired recess depth measured from the reference point; and
    etching down from a surface of the column of material until the endpoint is reached.

2. The method of claim 1, wherein obtaining the measured net reflectance spectrum comprises illuminating the portion of the substrate with a normal incident light beam.

3. The method of claim 1, wherein the reflectance of each of the n different regions is a weighted coherent sum of reflected fields from $k \geqq 1$ laterally-distinct areas constituting the region.

4. The method of claim 3, wherein each laterally-distinct area is modeled as a thin-film stack.

5. The method of claim 4, wherein computing the modeled net reflectance spectrum comprises modeling the substrate as having a nominally polarization-independent reflectance.

6. The method of claim 1 wherein determining the set of parameters comprises calculating a least squares difference error metric between the measured net reflectance spectrum and the modeled net reflectance spectrum and finding the set of parameters that minimizes the error metric.

7. The method of claim 6, Further comprising amplifying an effect of a change in the first dimension on the error metric.

8. The method of claim 7, wherein computing the modeled net reflectance spectrum comprises receiving as input a set of initial guesses for the set of parameters.

9. The method of claim 1, wherein the endpoint is based on a combination of broadband-reflectometry and an interferometric endpoint approach.

10. The method of claim 9, wherein computing the endpoint comprises computing a fringe count required to reach the endpoint.

11. The method of claim 10, wherein etching down comprises counting interference fringes evolved from the portion of the substrate during the etching and stopping the etching when the interference fringes evolved from the portion of the substrate have reached the fringe count.

12. The method of claim 1, further comprising determining a second dimension from the surface of the substrate to the surface of the column of material.

13. The method of claim 12, wherein determining the second dimension comprises extracting the second dimension from the set of parameters.

14. The method of claim 13, wherein computing the endpoint further comprises adjusting the endpoint by an amount proportional to the second dimension.

15. The method of claim 1, further comprising planarizing the surface of the substrate prior to determining the first dimension.

16. The method of claim 1, further comprising removing any native oxide buildup on the surface of the substrate prior to determining the first dimension.

17. A method of controlling a recess etch process, comprising:
    planarizing a surface of a multilayered substrate having a trench therein and a column of material deposited in the trench;
    after planarizing, determining a first dimension from the surface of the substrate to a reference point in the substrate by:
        obtaining a measured net reflectance spectrum of at least a portion of the substrate including the trench;
        computing a modeled net reflectance spectrum of the portion of the substrate as a weighted incoherent sum of reflectances from $n \geqq 1$ different regions constituting the portion of the substrate, wherein the reflectance of each of the n different regions is a weighted coherent sum of reflected fields from $k \geqq 1$ laterally-distinct areas constituting the region;
        determining a set of parameters that provides a close match between the measured net reflectance spectrum and the modeled net reflectance spectrum; and
        extracting the first dimension from the set of parameters;
    computing an endpoint of the recess etch process as a function of the first dimension and a desired recess depth measured from the reference point; and
    etching down from a surface of the column of material until the endpoint is reached.

18. The method of claim 17, further comprising determining a second dimension from the surface of the substrate to the surface of the column of material, wherein determining the second dimension comprises extracting the second dimension from the set of parameters, and wherein computing the endpoint further comprises adjusting the endpoint by an amount proportional to the second dimension.

19. A method of controlling a recess etch process, comprising:
    for a multilayered substrate having a trench therein and a column of material deposited in the trench, determining a first dimension from a surface of the substrate to a reference point in the substrate and a second dimension from the surface of the substrate to a surface of the column of material by:

obtaining a measured net reflectance spectrum of at least a portion of the substrate including the trench;

computing a modeled net reflectance spectrum of the portion of the substrate as a weighted incoherent sum of reflectances from $n \geq 1$ different regions constituting the portion of the substrate;

determining a set of parameters that provides a close match between the measured net reflectance spectrum and the modeled net reflectance spectrum; and extracting the first and second dimensions from the set of parameters;

computing an endpoint of the recess etch process as a function of the first and second dimensions and a desired recess depth measured from the reference point; and etching down from a surface of the column of material until the endpoint is reached.

20. The method of claim 17 wherein the weighted incoherent sum of reflectances is $$R = w_1(\lambda_0)|E_1|^2 + w_2(\lambda_0)|E_2|^2 + \ldots + w_n(\lambda_0)|E_n|^2$$

where R is the net reflectance measured, $E_n$ are the individual incoherently adding field terms, and $w_{n(\lambda_0)}$ are the weighting factors for the incoherently adding terms.

21. The method of claim 17 wherein the weighted coherent sums of reflected fields is $$E_1 = a_1(\lambda_0)E_{c1} + a_2(\lambda_0)e_{c1} + \ldots + a_k(\lambda_0)E_{ck}$$

where $a_1(\lambda_0)$ are the weighting factors for coherently adding field terms $E_{ck}$.

* * * * *